United States Patent
Xu et al.

(10) Patent No.: US 8,802,907 B2
(45) Date of Patent: *Aug. 12, 2014

(54) DEHYDROGENATION PROCESS

(75) Inventors: Teng Xu, Houston, TX (US); Edward A. Lemon, Jr., Easton, PA (US); Tan-Jen Chen, Kingwood, TX (US); Terry E. Helton, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 100 days.

This patent is subject to a terminal disclaimer.

(21) Appl. No.: 13/516,401

(22) PCT Filed: Dec. 17, 2010

(86) PCT No.: PCT/US2010/061022
§ 371 (c)(1), (2), (4) Date: Jul. 12, 2012

(87) PCT Pub. No.: WO2011/096995
PCT Pub. Date: Aug. 11, 2011

(65) Prior Publication Data
US 2012/0271079 A1    Oct. 25, 2012

Related U.S. Application Data

(60) Provisional application No. 61/301,799, filed on Feb. 5, 2010, provisional application No. 61/301,794, filed on Feb. 5, 2010, provisional application No. 61/334,767, filed on May 14, 2010.

(51) Int. Cl.
C07C 2/64 (2006.01)
C07C 2/66 (2006.01)
C07C 5/31 (2006.01)
C07C 2/74 (2006.01)
C07C 5/367 (2006.01)

(52) U.S. Cl.
CPC .............. *C07C 5/31* (2013.01); *C07C 2101/14* (2013.01); *C07C 2529/12* (2013.01); *C07C 2529/76* (2013.01); *C07C 2529/14* (2013.01); *C07C 2/74* (2013.01); *C07C 5/367* (2013.01); *C07C 2529/44* (2013.01); *C07C 2529/74* (2013.01); *C07C 2529/46* (2013.01)
USPC ........... 585/316; 585/314; 585/318; 585/319; 585/320; 585/323

(58) Field of Classification Search
USPC .................. 585/316, 314, 318, 319, 320, 323
See application file for complete search history.

(56) References Cited

U.S. PATENT DOCUMENTS

| | | |
|---|---|---|
| 3,308,069 A | 3/1967 | Wadlinger et al. |
| 3,412,165 A | 11/1968 | Slaugh et al. |
| 3,761,428 A | 9/1973 | Sugier et al. |
| RE28,341 E | 2/1975 | Wadlinger et al. |
| 3,962,362 A | 6/1976 | Suggitt |
| 4,094,918 A | 6/1978 | Murtha et al. |
| 4,122,125 A | 10/1978 | Murtha et al. |
| 4,147,726 A | 4/1979 | Wu |
| 4,177,165 A | 12/1979 | Murtha et al. |
| 4,206,082 A | 6/1980 | Murtha et al. |
| 4,501,926 A | 2/1985 | LaPierre et al. |
| 4,891,458 A | 1/1990 | Innes et al. |
| 5,053,571 A | 10/1991 | Makkee |
| 5,811,624 A | 9/1998 | Hantzer et al. |
| 5,906,729 A | 5/1999 | Chou |
| 6,037,513 A | 3/2000 | Chang et al. |
| 6,489,529 B1 | 12/2002 | Cheng et al. |
| 7,563,358 B2 | 7/2009 | Stavens et al. |
| 7,579,511 B1 | 8/2009 | Dakka et al. |
| 7,605,107 B2 | 10/2009 | Soled et al. |
| 2003/0083527 A1 | 5/2003 | Kuhnle et al. |
| 2006/0166809 A1 | 7/2006 | Malek et al. |
| 2011/0037022 A1 | 2/2011 | Dakka et al. |
| 2011/0288341 A1 | 11/2011 | Chen et al. |

FOREIGN PATENT DOCUMENTS

| | | |
|---|---|---|
| CS | 177505 | 7/1977 |
| EP | 0 323 192 | 7/1989 |
| EP | 0 338 734 | 10/1989 |
| GB | 720 064 | 12/1954 |
| GB | 1 454 717 | 11/1976 |
| JP | 54-099788 | 8/1979 |
| JP | 60-204370 | 10/1985 |
| WO | WO91/06616 | 5/1992 |
| WO | 2009/131769 | 10/2009 |
| WO | 2010/042261 | 4/2010 |

OTHER PUBLICATIONS

Borodina, I.B. et al., "*Hydroalkylation of Benzene and Ethylbenzene Over Metal Containing Zeolite Catalysts*", Microporous and Mesoporous Materials, 2007, vol. 105, No. 1-2, pp. 181-188.
Koel, B.E. et al. "*Thermochemistry of the Selective Dehydrogenation of Cyclohexane to Benzene on Pt Surfaces*", Journal of Molecular Catalysis: A Chemical, 1998, vol. 131, pp. 39-53.
Du et al., "*The Chemistry of Selective Ring-Opening Catalysts*", Applied Catalysis A: General, 2005, vol. 294, No. 1, pp. 1-21.
Galperin et al., "*Effect of Support Acid-Basic Properties on Activity and Selectivity of Pt Catalysts in Reaction of Methylcyclopentane Ring Opening*", Applied Catalysis A: General, 2003, vol. 239, No. 1-2, pp. 297-304.

(Continued)

*Primary Examiner* — Thuan D Dang
(74) *Attorney, Agent, or Firm* — Jamie L. Sullivan; Siwen Chen

(57) ABSTRACT

A processes for producing a dehydrogenation reaction product stream comprising the step of contacting a hydrocarbon stream comprising cyclohexane and methyl cyclopentane with a dehydrogenation catalyst comprising at least one metal or compound thereof and at least one molecular sieve and under conditions effective to convert at least a portion of the cyclohexane to benzene and to convert at least a portion of the methyl cyclopentane to at least one paraffin. The hydrocarbon stream is produced by hydroalkylating benzene and hydrogen to form a hydroalkylation reaction product stream which is separated to yield the hydrocarbon stream.

25 Claims, 2 Drawing Sheets

(56) References Cited

OTHER PUBLICATIONS

Gault, "*Mechanisma of Skeletal Isomerization of Hydrocarbons on Metals*", Advances in Catalysis, 1981, vol. 30, pp. 1-95.

Gonzales-Cortes et al., "*Tuning the Ring-Opening Reaction of 1,3-dimethylcyclohexane with the Addition of Potassium Over Ir-Containing Catalysts*", Chemical Engineering Journal, 2008, vol. 139, pp. 147-156.

Smirniotis et al., "*Comparison Between Zeolite β and γ-$Al_2O_3$ Supported PT for Reforming Reactions*", Journal of Catalysis, 1993, vol. 140, pp. 526-542.

Smirniotis et al., "*Increased Aromatization in the Reforming of Mixtures of N-Hexane, Methylcyclopentane and Methylcyclohexane Over Composites of Pt/BaKL Zeolite with Pt/beta or Pt/USY Zeolites*", Applied Catalysis A: General, 1995, vol. 123, No. 1, pp. 59-88.

Soled et al., "*Supported Metal Catalysts: Some Interesting New Leads in an Old Field*", Scientific Bases for the Preparation of Heterogeneous Catalysts, 2006, vol. 162, pp. 103-110.

Koshel et al. "*A Commercial Synthesis of Phenylcyclohexane ((PHCH)) by the Hydrodimerization of Benzene*", Neftekhimiya, 1977, vol. 17, pp. 705-709.

DEHYDROGENATION PROCESS

PRIORITY CLAIMS

This application is a National Stage Application of International Application No. PCT/US2010/061022 filed Dec. 17, 2010, which claims priority to U.S. Provisional Application Ser. No. 61/301,794 filed Feb. 5, 2010; U.S. Provisional Application Ser. No. 61/301,799 filed Feb. 5, 2010; and U.S. Provisional Application Ser. No. 61/334,767 filed May 14, 2010, the disclosures of which are fully incorporated herein by their reference.

CROSS REFERENCE TO RELATED APPLICATIONS

This patent application is related to U.S. Provisional Application Ser. No. 61/334,775, filed May 14, 2010; U.S. Provisional Application Ser. No. 61/334,781, filed May 14, 2010; U.S. Provisional Application Ser. No. 61/334,784, filed May 14, 2010; and U.S. Provisional Application Ser. No. 61/334,787, filed May 14, 2010, the disclosures of which are fully incorporated herein by their reference.

FIELD

The present invention relates to a process for dehydrogenating hydrocarbon streams and in particular the $C_6$-rich streams produced in the hydroalkylation of benzene to produce cyclohexylbenzene.

BACKGROUND

Various dehydrogenation processes have been proposed to dehydrogenate non-aromatic six membered ring compounds. These dehydrogenation processes are typically used to convert non-aromatic compounds such as cyclohexane into aromatic compounds such as benzene wherein the aromatic compound produced may be used as a raw material in a subsequent process. Alternatively, the aromatic compound produced may be used as a raw material in the same process which produced the non-aromatic compound to be dehydrogenated. For example, the dehydrogenation of cyclohexane to benzene can be important in the hydroalkylation process for producing cyclohexylbenzene as illustrated below.

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low particularly at economically viable benzene conversion rates and that large quantities of unwanted by-products, particularly cyclohexane and methylcyclopentane, were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a hydrogen to benzene molar ratio of about 0.01 to 100 and a weight hourly space velocity (WHSV) of about 0.01 to 100 hr$^{-1}$. The '513 patent discloses that the resultant cyclohexylbenzene can then be oxidized to the corresponding hydroperoxide and the peroxide decomposed to the desired phenol and cyclohexanone.

Not only does production of impurities such as cyclohexane and methylcyclopentane represent loss of valuable benzene feed, but also overall benzene conversion rates are typically only 40 to 60 wt % so that recycle of unreacted benzene is essential. Unless removed, these impurities will tend to build up in the recycle stream thereby displacing benzene and increasing the production of undesirable by-products. Thus a significant problem facing the commercial application of cyclohexylbenzene as a phenol precursor is removing the cyclohexane and methylcyclopentane impurities in the benzene recycle streams.

One solution to this problem is proposed in U.S. Pat. No. 7,579,511 which describes a process for making cyclohexylbenzene in which benzene undergoes hydroalkylation in the presence of a first catalyst to form a first effluent stream containing cyclohexylbenzene, cyclohexane, methyl cyclopentane, and unreacted benzene. The first effluent stream is then separated into a cyclohexane/methylcyclopentane-rich stream, a benzene-rich stream, and a cyclohexylbenzene-rich stream and the cyclohexane/methylcyclopentane-rich stream is contacted with a second, low acidity, dehydrogenation catalyst to convert at least a portion of the cyclohexane to benzene and at least a portion of the methylcyclopentane to linear and/or branched paraffins and form a second effluent stream. The benzene-rich stream and the second effluent stream can then be recycled to the hydroalkylation step. However, one problem with this process is that cyclohexane and methylcyclopentane have similar boiling points to that of benzene so that their separation by conventional distillation is difficult.

Another solution is proposed in International Patent Publication No. WO2009/131769, in which benzene undergoes hydroalkylation in the presence of a first catalyst to produce a first effluent stream containing cyclohexylbenzene, cyclohexane, and unreacted benzene. The first effluent stream is then divided into a cyclohexylbenzene-rich stream and a $C_6$ product stream comprising cyclohexane and benzene. At least part of said $C_6$ product stream is then contacted with a second catalyst under dehydrogenation conditions to convert at least part of the cyclohexane to benzene and produce a second effluent stream which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group VIII metal on a porous inorganic support such as aluminum oxide, silicon oxide, titanium oxide, zirconium oxide, activated carbon and combinations thereof. However, in practice, such a dehydrogenation catalyst has only limited activity for the conversion of methylcyclopentane and in some instances can undergo rapid aging. There is therefore a need for an improved catalyst for removing cyclohexane and methylcyclopentane from the benzene recycle streams employed in benzene hydroalkylation processes.

According to the present invention, it has now been found that acidic molecular sieves containing at least one dehydrogenation metal are effective catalysts for the dehydrogenation of cyclohexane to benzene and methylcyclopentane to linear and/or branched paraffins in benzene-containing and other hydrocarbon streams in that they exhibit high activity for the conversion of both five- and six-membered non-aromatic rings and yet have a relatively low aging rate.

SUMMARY

In one aspect, the invention resides in a dehydrogenation process comprising:

(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and benzene;

(b) dividing at least a portion of the hydroalkylation reaction product stream into a cyclohexylbenzene-rich stream and a $C_6$-rich stream comprising cyclohexane, methyl cyclopentane, and benzene; and (c) producing a dehydrogenation reaction product stream comprising the step of contacting at least a portion of the $C_6$-rich stream with a dehydrogenation catalyst comprising at least one metal or compound thereof and at least one molecular sieve and under conditions effective to convert at least a portion of the cyclohexane to benzene and to convert at least a portion of the methyl cyclopentane to at least one paraffin.

Conveniently, said at least one molecular sieve is selected from an aluminosilicate, an aluminophosphate, and a silicoaluminophosphate.

Conveniently, said at least one molecular sieve comprises an aluminosilicate having a silicon to aluminum atomic ratio greater than 5:1 and less than 300:1.

In one embodiment, said at least one molecular sieve has an average pore size of about 5 to about 7 Å, such as an AEL, AFI, MWW, MFI, MEL, MFS, MEI, MTW, EUO, MTT, HEU, FER, and/or TON structure type molecular sieve, especially ZSM-5 and/or ZSM-12.

In another embodiment, said at least one molecular sieve has an average pore size in excess of 7 Å, such as a VFI, LTL, MAZ, MEI, FAU, EMT, OFF, *BEA, MTW, MWW, and/or MOR structure type molecular sieve, especially Ultrastable Y (USY) and/or zeolite beta.

Conveniently, said at least one dehydrogenation metal is selected from Groups 6 to 10 of the Periodic Table of the Elements, especially platinum, palladium, ruthenium, nickel, zinc, tin, cobalt and mixtures thereof.

Conveniently, said dehydrogenation catalyst has an alpha value from about 0.5 to about 200, about 1 to about 100, and about 2 to about 80.

Conveniently, said conditions in the contacting (b) comprise a temperature between about 200° C. and about 550° C., a pressure between about 100 and about 7,000 kPaa, and a hydrogen to hydrocarbon stream molar ratio between 0.1 and 10.

In another aspect, the invention resides in a process for producing cyclohexylbenzene, the process comprising:

(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;

(b) separating at least a portion of the hydroalkylation reaction product stream into (i) a $C_6$-rich stream comprising benzene, cyclohexane, and methylcyclopentane and (ii) a cyclohexylbenzene-rich stream;

(c) contacting at least a portion of said $C_6$-rich stream with a dehydrogenation catalyst comprising at least one dehydrogenation metal or compound thereof and at least one molecular sieve, said contacting being conducted under conditions effective to convert at least a portion of the cyclohexane to benzene and at least a portion of the methylcyclopentane to at least one paraffin and form a dehydrogenation reaction product stream;

(d) separating at least a portion of said dehydrogenation reaction product stream produced into a $C_6$ recycle stream and a paraffins-rich stream;

(e) recycling at least a portion of the said $C_6$ recycle stream to (a); and (f) recovering cyclohexylbenzene from said cyclohexylbenzene-rich stream.

Conveniently, said at least one molecular sieve is selected from a large pore molecular sieve and an intermediate pore size molecular sieve.

Conveniently, said hydroalkylation conditions include a temperature between about 100° C. and about 400° C. and a pressure between about 100 and about 7,000 kPa.

Conveniently, wherein the hydrogen and benzene are fed to said contacting (a) in a molar ratio of hydrogen to benzene of between about 0.15:1 and about 15:1.

Conveniently, hydrogen and benzene are fed to said contacting (a) in a molar ratio of hydrogen to benzene of between about 0.15:1 and about 15:1.

Conveniently, said hydroalkylation catalyst comprises a molecular sieve of the MCM-22 family and a hydrogenation metal.

DETAILED DESCRIPTION

Figure 1:
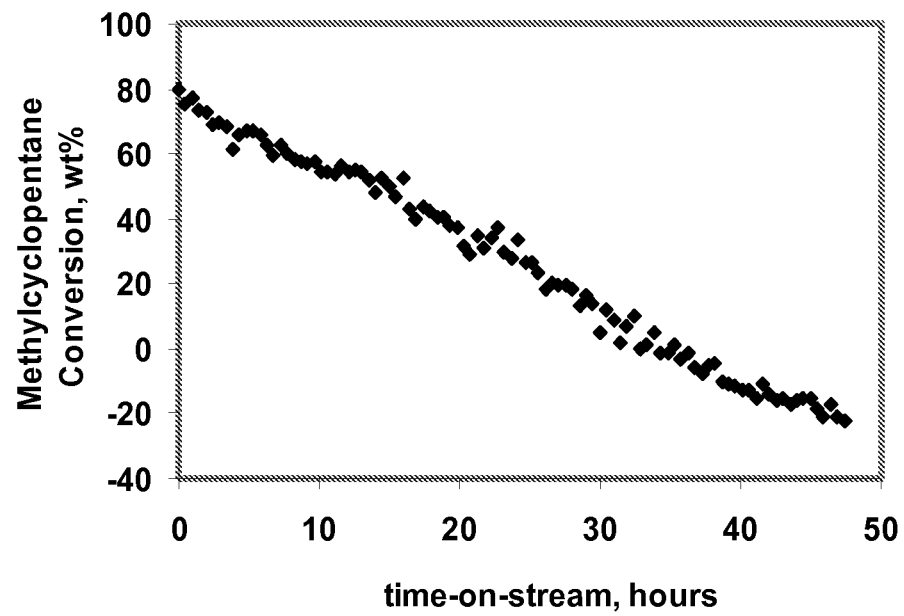
FIG. 1 is a graph of methylcyclopentane (MCP) conversion against time-on-stream at 500° C., 10 hr$^{-1}$ WHSV, 2/1 H$_2$/feed molar ratio, and 100 psig (689 kpag) using the 0.3 wt % Pt/alumina catalyst of Example 1.

Described herein is a process for dehydrogenating a hydrocarbon stream comprising at least one non-aromatic six-membered ring compound and at least one non-aromatic five-membered ring compound and optionally at least one aromatic compound, such as benzene. The process comprises contacting at least a portion of the hydrocarbon stream with a dehydrogenation catalyst under conditions effective to convert at least a portion of the at least one non-aromatic six-membered ring compound in the hydrocarbon stream to benzene and to convert at least a portion of the at least one five-membered ring compound in the hydrocarbon stream to at least one paraffin and form a dehydrogenation reaction product stream.

In one embodiment, the hydrocarbon stream comprises at least 10 wt % benzene, at least 20 wt % benzene, at least 30 wt % benzene, at least 40 wt % benzene, at least 50 wt % benzene, at least 60 wt % benzene, at least 70 wt % benzene, and at least 80 wt % benzene. In another embodiment, the hydrocarbon stream comprises at least 1 wt % cyclohexane, at least 5 wt % cyclohexane, at least 10 wt % cyclohexane, and at least 20 wt % cyclohexane. In still another embodiment, the hydrocarbon stream comprises at least 0.05 wt % methylcyclopentane, at least 0.5 wt % methylcyclopentane, and 5 wt % methylcyclopentane.

The dehydrogenation catalyst employed in the present process comprises at least one dehydrogenation metal or a compound thereof and at least one molecular sieve.

Suitable dehydrogenation metals for use in the catalyst comprise metals from Groups 6 to 10 of the Periodic Table of the Elements, especially platinum, palladium, ruthenium, nickel, zinc, tin, cobalt and mixtures thereof. As used herein, the numbering scheme for the Periodic Table Groups is as disclosed in Chemical and Engineering News, 63(5), 27 (1985).

The molecular sieve of the dehydrogenation catalyst can be an aluminosilicate, an aluminophosphate, a silicoaluminophosphate, or a combination thereof. Generally the molecular sieve is an aluminosilicate typically with a silicon to aluminum atomic ratio greater than 5:1 and less than 300:1.

Usually the molecular sieve will be incorporated with binder material such as clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia.

In one embodiment, the at least one molecular sieve is a large pore molecular sieve having an average pore size in excess of 7 Å or from 7 Å to 12 Å in other embodiments. Suitable large pore molecular sieves include those having the structure types VFI, LTL, MAZ, MEI, FAU, EMT, OFF, *BEA, MTW, MWW, and MOR (see IUPAC Commission of Zeolite Nomenclature and the "Atlas of Zeolite Framework Types", eds. Ch. Baerlocher, L. B. McCusker, and D. H. Olson, Elsevier, Sixth Revised Edition, 2007, which is hereby incorporated by reference). Examples of specific large pore molecular sieves include Zeolite L, Zeolite Beta, Zeolite Y, Ultrastable Y (USY), Dealuminized Y (Deal Y), Mordenite, ZSM-3, ZSM-4, ZSM-18, ZSM-20, ZSM-12, MCM-22, and faujasite. Preferred large pore zeolites are mordenite, Ultrastable Y (USY) and zeolite beta. USY is described in detail in U.S. Pat. Nos. 3,293,192 and 3,402,996; and Zeolite Beta is described in detail in U.S. Pat. No. 3,308,069 and U.S. Pat. No. Re 28,341, all of which are hereby incorporated by reference.

In another embodiment, the at least one molecular sieve is a medium pore molecular sieve having an average pore size of about 5 to about 7 Å. Suitable medium pore molecular sieves include those having the structure types MFI, MEL, MTW, EUO, MTT, HEU, FER, MFS, and TON structure type zeolites. Examples of specific intermediate pore size molecular sieves include ZSM-5, ZSM-12, ZSM-22, ZSM-23, ZSM-34, ZSM-35, ZSM-38, ZSM-48, ZSM-50, and ZSM-57. Preferred medium pore zeolites are ZSM-5 and ZSM-12. ZSM-5 is described in detail in U.S. Pat. No. 3,702,886 and RE 29,948 and ZSM-12 is described in U.S. Pat. No. 3,832,449, all of which are hereby incorporated by reference.

The dehydrogenation catalyst employed herein has an alpha value from about 0 to less than 200, from about 1 to about 100, such as from about 2 to about 80, and from about 0 to about 1. The alpha value is a measure of the acidic functionality of the catalyst and is described together with details of its measurement in U.S. Pat. No. 4,106,218 and in J. Catalysis, Vol. VI, pp. 278-287 (1966) and reference is made to these for such details. Higher alpha values correspond with a more active cracking catalyst. Where necessary the alpha value of the catalyst can be adjusted by methods known in the art, for example by steaming.

Preferably, the alpha value is from about 0 to about 200 and from about 0.5 to about 150. In other embodiments, the alpha value lower limit may be about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, and about 10; and the upper alpha value limit may be about 200, about 175, about 150, about 125, about 100, about 90, about 80, about 70, about 60, about 50, about 40, about 30, about 20, about 10, about 5, about 1.9, about 1.8, about 1.7, about 1.6, about 1.5, about 1.4, about 1.3, about 1.2, about 1.1, about 1, about 0.9, about 0.8, about 0.7, about 0.6, and about 0.5 with ranges from any lower limit to any upper limit being contemplated.

The dehydrogenation process is generally conducted at a temperature between about 200° C. and about 550° C., such as between about 300° C. and about 500° C., a pressure between about 100 and about 7,000 kPaa, such as between about 300 and about 3000 kPaa, a weight hourly space velocity (WHSV) between about 0.2 and about 50 $hr^{-1}$, such as between about 1 and about 20 $hr^{-1}$ and a hydrogen to hydrocarbon feed molar ratio between about 0.1 and about 10, such as between about 1 and about 5.

The conversion of methylcyclopentane (MCP) was calculated using the following formula:

MCP conversion in wt %=[(wt % of MCP in the feed− wt % of MCP in effluent)/(wt % of MCP in the feed)]*100.

The dehydrogenation process generally yields a MCP conversion in wt % at 500° C. of greater than 20%, greater than 30%, greater than 40%, greater than 50%, greater than 60%, greater than 70%, greater than 80%.

Although the present process can be used with any hydrocarbon stream comprising at least one non-aromatic six-membered ring compound and at least one non-aromatic five-membered ring compound, the process has particular application as part of an integrated process for the conversion of benzene to phenol. In such an integrated process the benzene is initially converted to cyclohexybenzene by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

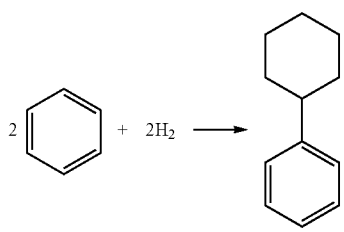
(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is generally a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56, and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2 wt % respectively. The hydroalkylation reaction effluent is therefore fed to a separation system normally comprising at least two distillation towers. Given the similar boiling points of benzene, cyclohexane, and methylcyclopentane, it is difficult to separate these materials by distillation. Thus, in a distillation tower, a $C_6$-rich stream comprising benzene, cyclohexane, and methylcyclopentane is recovered from the hydroalkylation reaction effluent. This $C_6$-rich stream is then subjected to the dehydrogenation process described above such that at least a portion of the cyclohexane in the stream is converted to benzene and at least a portion of the methylcyclopentane is converted to linear and/or branched paraffins, such as 2-methylpentane, 3-methylpentane, n-hexane, and other hydrocarbon components such as isohexane, $C_5$ aliphatics, and $C_1$ to $C_4$ aliphatics. The dehydrogenation product stream is then fed to a further separation system, typically a further distillation tower, to divide the dehydrogenation product stream into a $C_6$ recycle stream and a paraffin-rich stream comprising 2-methylpentane, 3-methylpentane, and other $C_1$ to $C_6$ paraffins. The $C_6$ recycle stream can then be recycled to the hydroalkylation step, while the paraffinic stream can be used as a fuel for the process.

After separation of the $C_6$-rich stream, the remainder of hydroalkylation reaction effluent is fed a second distillation tower to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1. The transalkylation reaction effluent can then be returned to the second distillation tower to recover the additional monocyclohexylbenzene product produced in the transalkylation reaction.

After separation in the second distillation tower, the cyclohexylbenzene is converted into phenol by a process similar to the Hock process. In this process, the cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst can be used in this reaction.

Suitable dehydrogenation catalysts include a dehydrogenation catalyst comprising (i) a dehydrogenation component comprising a Group 6 to Group 10 metal component and (ii) a metal promoter comprising a Group 1 or Group 2 metal component. The dehydrogenation catalyst may be produced by initially treating the support, such as by impregnation, with a solution of the metal promoter, such as an aqueous solution of potassium carbonate. After drying, the treated support is calcined, normally in an oxygen-containing atmosphere, such as air, at a temperature of about 100° C. to about 700° C. for a time of about 0.5 to about 50 hours. The calcined support is then treated, again typically by impregnation, with a solution of the dehydrogenation component or a precursor thereof.

Suitable conditions for the dehydrogenation step comprise a temperature of about 250° C. to about 500° C. and a pressure of about 0.01 atm to about 20 atm (1 kPa to 2000 kPa), such as a temperature of about 300° C. to about 450° C. and a pressure of about 1 atm to about 10 atm (100 kPa to 300 kPa).

Provided are one or more embodiments:

A. A dehydrogenation process comprising:
(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and benzene;
(b) dividing at least a portion of the hydroalkylation reaction product stream into a cyclohexylbenzene-rich stream and a $C_6$-rich stream comprising cyclohexane, methyl cyclopentane, and benzene; and
(c) producing a dehydrogenation reaction product stream comprising the step of contacting at least a portion of the $C_6$-rich stream with a dehydrogenation catalyst comprising at least one metal or compound thereof and at least one molecular sieve and under conditions effective to convert at least a portion of the cyclohexane to benzene and to convert at least a portion of the methyl cyclopentane to at least one paraffin.

B. The process of embodiment A, wherein the dehydrogenation catalyst has an alpha value from about 0.5 to about 200.

C. The process of any one of embodiments A and B, wherein the dehydrogenation catalyst has an alpha value from about 5 to about 100.

D. The process of any one of the preceding embodiments, wherein the dehydrogenation catalyst has an alpha value from about 10 to about 80.

E. The process of any one of the preceding embodiments, wherein the at least one molecular sieve is selected from an aluminosilicate, an aluminophosphate, and a silicoaluminophosphate.

F. The process of any one of the preceding embodiments, wherein the at least one molecular sieve comprises an aluminosilicate having a silicon to aluminum atomic ratio greater than 5:1 and less than 300:1.

G. The process any one of the preceding embodiments, wherein the at least one molecular sieve has an average pore size of about 5 to about 7 Å.

H. The process of any one of the preceding embodiments, wherein the at least one molecular sieve comprises an AEL, AFI, MWW, MFI, MEL, MFS, MEI, MTW, EUO, MTT, HEU, FER, and/or TON structure type molecular sieve.

I. The process of any one of the preceding embodiments, wherein the at least one molecular sieve comprises ZSM-5 and/or ZSM-12.

J. The process of any one of the preceding embodiments, wherein the at least one molecular sieve has an average pore size in excess of 7 Å.

K. The process of any one of the preceding embodiments, wherein the at least one molecular sieve comprises a VFI, LTL, MAZ, MEI, FAU, EMT, OFF, *BEA, MTW, MWW, and/or MOR structure type molecular sieve.

L. The process of any one of the preceding embodiments, wherein the at least one molecular sieve comprises Ultrastable Y (USY) and/or zeolite beta.

M. The process of any one of the preceding embodiments, wherein the at least one metal is selected from Groups 6 to 10 of the Periodic Table of the Elements.

N. The process of any one of the preceding embodiments, wherein the at least one metal is selected from platinum, palladium, ruthenium, nickel, zinc, tin, and cobalt.

O. The process of any one of the preceding embodiments, wherein the conditions in the contacting producing step (c) comprise a temperature between about 200° C. and about 550° C., a pressure between about 100 and about 7,000 kPaa.

P. The process of any one of the preceding embodiments, wherein the $C_6$-rich stream comprises at least 70 wt % benzene, at least 5 wt % cyclohexane, and at least 0.1 wt % methylcyclopentane.

Q. The process of any one of the preceding embodiments wherein the conversion of the methylcyclopentane is greater than 50%.

R. The process any one of the preceding embodiments and further comprising
(d) separating at least a portion of the dehydrogenation reaction product stream produced in the producing step (c) into a benzene recycle stream and a paraffin-rich stream comprising 2-methylpentane and 3-methylpentane; and
(e) recycling at least a portion of the benzene recycle stream to the contacting step (a).

S. A process for producing cyclohexylbenzene, the process comprising:
(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;
(b) dividing at least a portion of the hydroalkylation reaction product stream into (i) a $C_6$-rich stream comprising benzene, cyclohexane, and methylcyclopentane and (ii) a cyclohexylbenzene-rich stream;
(c) producing a dehydrogenation reaction product stream comprising the step of contacting at least a portion of the $C_6$-rich stream with a dehydrogenation catalyst comprising at least one dehydrogenation metal or compound thereof and at least one molecular sieve and the contacting being conducted under conditions effective to convert at least a portion of the cyclohexane to benzene and at least a portion of the methylcyclopentane to at least one paraffin;
(d) separating at least a portion of the dehydrogenation reaction product stream produced into a benzene recycle stream and a paraffins-rich stream comprising 2-methylpentane and 3-methylpentane;
(e) recycling at least a portion of the benzene recycle stream to the contacting step (a); and
(f) recovering cyclohexylbenzene from the cyclohexylbenzene-rich stream.

T. The process of embodiment S, wherein the at least one molecular sieve is selected from a large pore molecular sieve and an intermediate pore size molecular sieve.

U. The process of any one of embodiments S and T, wherein the dehydrogenation catalyst has an alpha value from about 0.5 to about 200.

V. The process of any one of embodiments S to U, wherein the dehydrogenation catalyst has an alpha value from about 5 to about 100.

W. The process of any one of embodiments S to V, wherein the hydroalkylation conditions in the contacting (a) include a temperature between about 100° C. and about 400° C. and a pressure between about 100 and about 7,000 kPa.

X. The process of any one of embodiments S to W, wherein the hydroalkylation catalyst comprises a molecular sieve of the MCM-22 family and a hydrogenation metal.

Y. The process of any one of embodiments S to X, wherein the conditions in the producing step (c) comprise a temperature between about 200° C. and about 550° C., a pressure between about 100 and about 7,000 kPaa.

When a stream is described as being "rich" in a specified species, it is meant that the specified species in that stream is enriched relative to other species in the same stream or composition on a weight percentage basis. For illustration purposes only, a cyclohexylbenzene-rich stream will have a cyclohexylbenzene wt % greater than any other species or component in that same stream. A "$C_6$" species generally means any species containing 6 carbon atoms.

The invention will now be more particularly described with reference to the following non-limiting Examples and the accompanying drawings.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Oxygen chemisorption measurements are obtained using the Micrometrics ASAP 2010. Approximately 0.3 to 0.5 grams of catalyst are into the Micrometrics. Under flowing helium, the catalyst is ramped from ambient to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen isotherm is collected in increments at 35° C. between 0.50 and 760 mm Hg.

EXAMPLE 1

Comparative

Preparation of 0.3 wt % Pt/Alumina Catalyst 100 grams of a commercial alumina extrudate was incipient wetness impregnated with 0.3 wt % platinum using an aqueous platinum tetraammine nitrate solution. After the incipient wetness impregnation, the 0.3 wt % containing alumina catalyst was dried overnight at 121° C. followed by calcination in air at 360° C. to convert the platinum tetraammine nitrate to platinum oxide. The oxygen chemisorption on the final catalyst was 57%.

EXAMPLE 2

Preparation of 0.6 wt % Pt/Zeolite Beta Catalyst

A zeolite beta extrudate was prepared by extruding 65 parts ammonium form of zeolite beta (100% solids) with 35 parts pseudoboehmite alumina (100% solids). The dried extrudate was calcined in a nitrogen/air mixture to decompose the organic template and convert the ammonium beta to H-form. The shape and diameter of the beta extrudate was 1/20" (1.27 mm) quadrulobe. The air calcined beta catalyst was steamed in 100% steam to reduce the alpha activity to a range of 30 to 55. After steaming, the H-form of the beta extrudate was ion exchanged with platinum tetraammine chloride (target 0.6 wt % Pt). After ion exchange, the platinum tetraammine chloride beta extrudate was washed with deionized water to remove residual chloride prior to calcination in air. After washing, the 0.6 wt % Pt alumina bound beta catalyst was calcined in air to convert the platinum salt to platinum oxide. The final catalyst composition was 0.6 wt % Pt on 65 wt % Beta, 35 wt % alumina extrudate.

EXAMPLE 3

Comparative

Performance of 0.3 wt % Pt/Alumina Catalyst

The extrudate catalyst of Example 1 was cut into particles of L/D=1 (length/diameter). 250 mg of catalyst was then mixed with 250 mg of 40 mesh (0.42 mm) quartz chips, and the mixture was packed into a ¼" (0.64 cm) stainless steel reactor. A liquid mixture of methylcyclopentane, cyclohexane and benzene was delivered to the reactor using an ISCO pump. The liquid feed was vaporized prior to mixing with $H_2$. The mixture ($H_2$ and vaporized feed) was fed into the downflow reactor. The reaction was typically run at 500° C. and 100 psig (689 kPag) total reactor pressure, 10 hr$^{-1}$ WHSV (based on total liquid feed) with a $H_2$/liquid feed molar ratio of 2. The liquid feed composition was 4.4 wt % methylcyclopentane (MCP), 18.5 wt % cyclohexane (CH), and 77.1 wt % benzene (Bz).

Prior to the introduction of the liquid feed, the catalyst was pretreated in 50 sccm $H_2$ at 100 psig (689 kPag) by ramping reactor temperature from room temperature to 460° C. at 2° C./min; the reactor temperature was held at 460° C. for 2 hours under the same $H_2$ flow and pressure.

The effluent from the reactor was sampled using a Valco sampling valve, and the sample was sent to an on-line GC equipped with a FID detector for analysis. All hydrocarbons were quantified and the results were normalized to 100%. $H_2$ was not included in the analysis. Conversion of methylcyclopentane (MCP) and cyclohexane (CH) was calculated using the following formulae:

MCP conversion in wt %=[(wt % of MCP in the feed [i.e., 4.4]–wt % of MCP in effluent)/(wt % of MCP in the feed [i.e., 4.4])]*100, and CH conversion in wt %=[(wt % of CH in the feed [i.e., 18.5]–wt % of CH in effluent)/(wt % of CH in the feed[i.e., 18.5])]*100.

Selectivity was calculated by normalizing all the products to 100% measured in the reactor effluent excluding MCP, CH and Bz. The selectivity data is reported as wt %. The results are shown in FIGS. 1 to 2.

Figure 2:
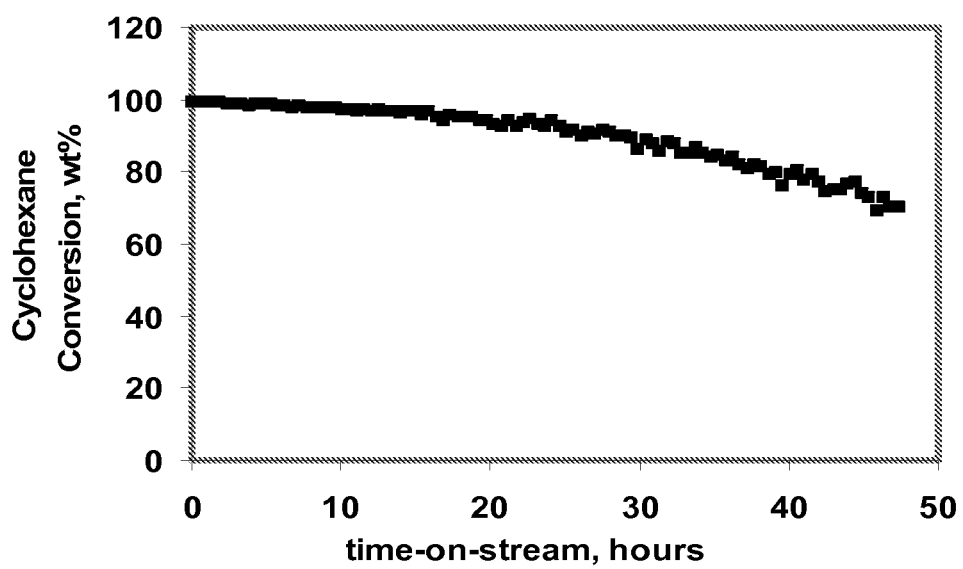
FIG. 2 is a graph of cyclohexane (CH) conversion against time-on-stream at 500° C., 10 hr$^{-1}$ WHSV, 2/1 H$_2$/feed molar ratio, and 100 psig (689 kpag) using the 0.3 wt % Pt/alumina catalyst of Example 1.

FIGS. 1 and 2 show plots of MCP and CH conversions vs. time-on-stream for the 0.3 wt % Pt/alumina catalyst, respectively, at 500° C., 10 hr$^{-1}$ WHSV, 2/1 $H_2$/feed molar ratio, and 100 psig (689 kpag). Note that MCP conversion started at about 80% on fresh catalyst, but decreased quite significantly as time-on-stream increased. After roughly 36 hours time-on-stream, the conversion of MCP was around zero. The catalyst produced more MCP than the feed mixture after 36 hours time-on-stream. Although the reaction mechanism for producing MCP is not fully known, we speculate that MCP was produced by the ring contraction of cyclohexane.

The conversion of cyclohexane was generally high when the catalyst was fresh, i.e., short time-on-stream. However, at around 36 hours time-on-stream, the conversion of cyclohexane decreased to around 84 wt %. At 47 hours time-on-stream, cyclohexane conversion further reduced to around 70 wt %, which is consistent with the observation of negative MCP conversion at longer time-on-stream since unconverted cyclohexane could be converted into MCP via six-member ring contraction.

The major products from the reaction of MCP were 2-methylpentane, 3-methylpentane, hexane, $C_1$-$C_4$, $C_5$, and heavies. Most of the products are readily separable from benzene via simple distillation. $C_{1-4}$, $C_5$ and heavies refer to hydrocarbons that have 1 to 4 carbons, five carbons, and hydrocarbons containing over 6 carbons, respectively. The $C_{1-4}$ and $C_5$ are mostly paraffins, while the heavies are mostly substituted benzenes such as xylene and bi-phenyl.

EXAMPLE 4

Performance of 0.6 wt % Pt/Zeolite Beta Catalyst

Figure 3:
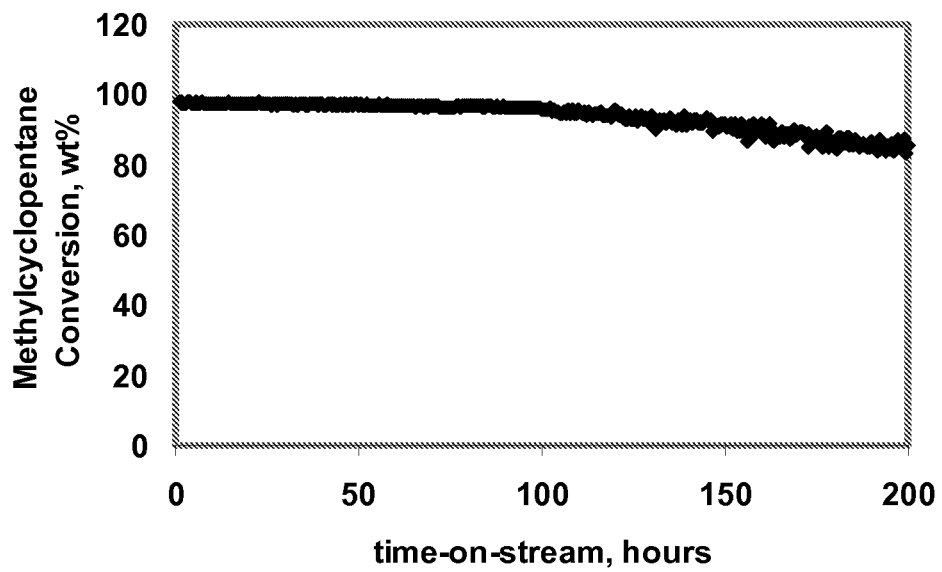
FIG. 3 is a graph of methylcyclopentane (MCP) conversion against time-on-stream at 500° C., 10 hr$^{-1}$ WHSV, 2/1 H$_2$/feed molar ratio, and 100 psig (689 kpag) using the 0.6 wt % Pt/beta catalyst of Example 2.
Figure 4:
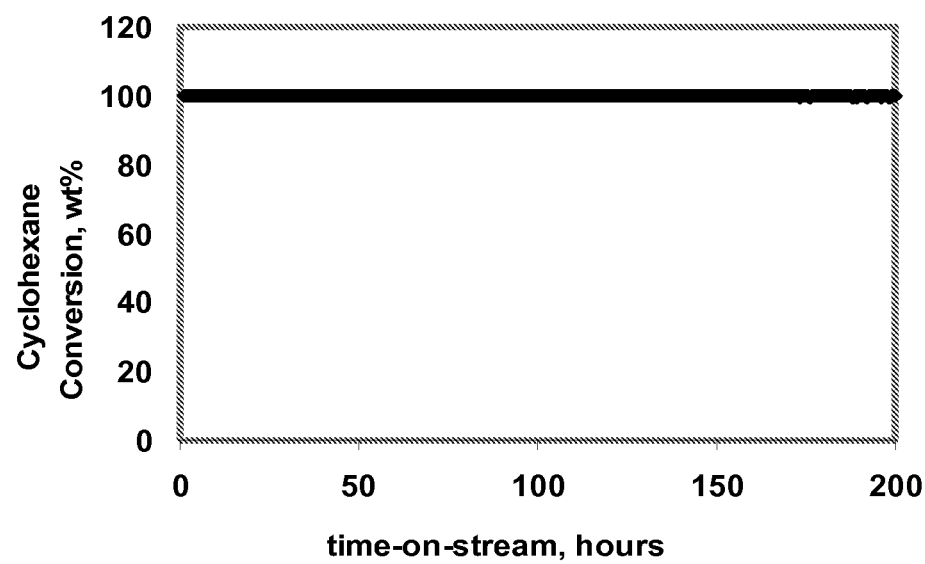
FIG. 4 is a graph of cyclohexane (CH) conversion against time-on-stream at 500° C., 10 hr$^{-1}$ WHSV, 2/1 H$_2$/feed molar ratio, and 100 psig (689 kpag) using the 0.6 wt % Pt/beta catalyst of Example 2.

The process of Example 3 was repeated using the 0.6 wt % Pt/zeolite beta catalyst of Example 2 and the results are shown in FIGS. 3 to 4.

FIGS. 3 and 4 show plots of MCP and CH conversions as a function of time-on-stream on a 0.6 wt % Pt/beta catalyst, respectively, at 500° C., 10 hr$^{-1}$ WHSV, 2/1 H$_2$/feed molar ratio, and 100 psig (689 kpag). Note that the 0.6 wt % Pt/beta catalyst was more stable, and more active than the 0.3 wt % Pt/alumina catalyst. For example, under identical experimental conditions, MCP conversion was close to 100% for at least the initial 100 hours time-on-stream. The conversion of MCP was more than 80% even after 200 hrs time-on-stream while the conversion of MCP was around zero at around 36 hrs on 0.3 wt % Pt/alumina catalyst.

FIG. 4 shows the conversion of cyclohexane as a function of time-on-stream on 0.6 wt % Pt/beta. The conversion of cyclohexane was essentially 100% even after 200 hours time-on-stream, which compared very favorably with the conversion of CH on 0.3 wt % Pt/alumina.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A dehydrogenation process comprising:
   (a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and benzene;
   (b) dividing at least a portion of the hydroalkylation reaction product stream into a cyclohexylbenzene-rich stream and a $C_6$-rich stream comprising cyclohexane, methyl cyclopentane, and benzene; and
   (c) producing a dehydrogenation reaction product stream comprising the step of contacting at least a portion of the $C_6$-rich stream with a dehydrogenation catalyst comprising at least one metal or compound thereof and at least one molecular sieve and under conditions effective to convert at least a portion of the cyclohexane to benzene and to convert at least a portion of the methyl cyclopentane to at least one paraffin.

2. The process of claim 1, wherein the dehydrogenation catalyst has an alpha value from about 0.5 to about 200.

3. The process of claim 1, wherein the dehydrogenation catalyst has an alpha value from about 5 to about 100.

4. The process of claim 1, wherein the dehydrogenation catalyst has an alpha value from about 10 to about 80.

5. The process of claim 1, wherein the at least one molecular sieve is selected from an aluminosilicate, an aluminophosphate, and a silicoaluminophosphate.

6. The process of claim 1, wherein the at least one molecular sieve comprises an aluminosilicate having a silicon to aluminum atomic ratio greater than 5:1 and less than 300:1.

7. The process of claim 1, wherein the at least one molecular sieve has an average pore size of about 5 to about 7 Å.

8. The process of claim 1, wherein the at least one molecular sieve comprises an AEL, AFI, MWW, MFI, MEL, MFS, MEI, MTW, EUO, MTT, HEU, FER, and/or TON structure type molecular sieve.

9. The process of claim 1, wherein the at least one molecular sieve comprises ZSM-5 and/or ZSM-12.

10. The process of claim 1, wherein the at least one molecular sieve has an average pore size in excess of 7 Å.

11. The process of claim 1, wherein the at least one molecular sieve comprises a VFI, LTL, MAZ, MEI, FAU, EMT, OFF, *BEA, MTW, MWW, and/or MOR structure type molecular sieve.

12. The process of claim 1, wherein the at least one molecular sieve comprises Ultrastable Y (USY) and/or zeolite beta.

13. The process of claim 1, wherein the at least one metal is selected from Groups 6 to 10 of the Periodic Table of the Elements.

14. The process of claim 1, wherein the at least one metal is selected from platinum, palladium, ruthenium, nickel, zinc, tin, and cobalt.

15. The process of claim 1, wherein the conditions in the contacting producing step (c) comprise a temperature between about 200° C. and about 550° C., a pressure between about 100 and about 7,000 kPaa.

16. The process of claim 1, wherein the $C_6$-rich stream comprises at least 70 wt % benzene, at least 5 wt % cyclohexane, and at least 0.1 wt % methylcyclopentane.

17. The process of claim 16, wherein the conversion of the methylcyclopentane is greater than 50%.

18. The process of claim 1, and further comprising:
   (d) separating at least a portion of the dehydrogenation reaction product stream produced in the producing step (c) into a benzene recycle stream and a paraffin-rich stream comprising 2-methylpentane and 3-methylpentane; and
   (e) recycling at least a portion of the benzene recycle stream to the contacting step (a).

19. A process for producing cyclohexylbenzene, the process comprising:
   (a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;
   (b) dividing at least a portion of the hydroalkylation reaction product stream into (i) a $C_6$-rich stream comprising benzene, cyclohexane, and methylcyclopentane and (ii) a cyclohexylbenzene-rich stream;
   (c) producing a dehydrogenation reaction product stream comprising the step of contacting at least a portion of the $C_6$-rich stream with a dehydrogenation catalyst comprising at least one dehydrogenation metal or compound thereof and at least one molecular sieve and the contacting being conducted under conditions effective to convert at least a portion of the cyclohexane to benzene and at least a portion of the methylcyclopentane to at least one paraffin;
(d) separating at least a portion of the dehydrogenation reaction product stream produced into a benzene recycle stream and a paraffins-rich stream comprising 2-methylpentane and 3-methylpentane;
(e) recycling at least a portion of the benzene recycle stream to the contacting step (a); and
(f) recovering cyclohexylbenzene from the cyclohexylbenzene-rich stream.

20. The process of claim 19, wherein the at least one molecular sieve is selected from a large pore molecular sieve and an intermediate pore size molecular sieve.

21. The process of claim 19, wherein the dehydrogenation catalyst has an alpha value from about 0.5 to about 200.

22. The process of claim 19, wherein the dehydrogenation catalyst has an alpha value from about 5 to about 100.

23. The process of claim 19, wherein the hydroalkylation conditions in the contacting (a) include a temperature between about 100° C. and about 400° C. and a pressure between about 100 and about 7,000 kPa.

24. The process of claim 19, wherein the hydroalkylation catalyst comprises a molecular sieve of the MCM-22 family and a hydrogenation metal.

25. The process of claim 19, wherein the conditions in the producing step (c) comprise a temperature between about 200° C. and about 550° C., a pressure between about 100 and about 7,000 kPaa.

* * * * *